US007773764B2

(12) United States Patent
Niederdränk

(10) Patent No.: US 7,773,764 B2
(45) Date of Patent: Aug. 10, 2010

(54) HEARING DEVICE WITH EAR CANAL MICROPHONE

(75) Inventor: Torsten Niederdränk, Erlangen (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1142 days.

(21) Appl. No.: 11/410,469

(22) Filed: Apr. 25, 2006

(65) Prior Publication Data

US 2006/0239485 A1 Oct. 26, 2006

(30) Foreign Application Priority Data

Apr. 25, 2005 (DE) ....................... 10 2005 019 148

(51) Int. Cl.
*H04R 25/00* (2006.01)
*A61N 1/00* (2006.01)

(52) U.S. Cl. ....................... 381/325; 381/326; 381/328; 607/57; 600/25

(58) Field of Classification Search ................. 381/328, 381/151, 322–326; 181/135; 607/57; 600/25
See application file for complete search history.

(56) References Cited

U.S. PATENT DOCUMENTS

| | | | | |
|---|---|---|---|---|
| 5,692,059 | A * | 11/1997 | Kruger | 381/151 |
| 6,164,409 | A * | 12/2000 | Berger | 181/135 |
| 6,643,378 | B2 * | 11/2003 | Schumaier | 381/326 |
| 7,471,800 | B2 * | 12/2008 | Neilson | 381/325 |
| 2005/0190938 | A1 * | 9/2005 | Shennib et al. | 381/328 |

FOREIGN PATENT DOCUMENTS

| | | |
|---|---|---|
| DE | 85 17 421 U1 | 9/1985 |
| DE | 41 28 172 C2 | 3/1993 |
| EP | 0 835 042 A2 | 4/1998 |

* cited by examiner

*Primary Examiner*—Brian Ensey
*Assistant Examiner*—Sunita Joshi

(57) ABSTRACT

A hearing device with a plastic mold arranged in the ear, in other words a hearing device shell or an otoplastic, features a loudspeaker in its interior. A cerumen protection system extends from the loudspeaker to the surface of the plastic mold. In accordance with the invention, a microphone is arranged in the cerumen protection system.

15 Claims, 1 Drawing Sheet

HEARING DEVICE WITH EAR CANAL MICROPHONE

CROSS REFERENCE TO RELATED APPLICATIONS

This application claims priority of German application No. 102005019148.7 filed Apr. 25, 2005, which is incorporated by reference herein in its entirety.

FIELD OF THE INVENTION

The invention relates to a hearing device, particularly to a hearing device with ear canal microphone.

BACKGROUND OF THE INVENTION

A hearing device which can be worn in the ear and features a loudspeaker and a cerumen protection system is known from U.S. Pat. No. 6,164,409.

A hearing device is further known from DE 41 28 172 C2, in which a second acoustic sensor is provided. This is inserted into the inner ear of the hearing device wearer, together with an electroacoustic converter (receiver).

With future hearing devices, a series of additional functions is conceivable for use by hearing impaired, in which one prerequisite is that the acoustic signal in the ear canal is recorded. Naturally however, there is only minimal space for a microphone in the plastic mold which can be inserted into the ear.

SUMMARY OF THE INVENTION

It is the object of the invention to make these additional functions available and at that same time ensure a compact design of the hearing device.

This invention is achieved in that a microphone is arranged in the cerumen protection system.

The invention is based on the fact that even with in-the-ear hearing devices it is possible to ensure that sufficient space is available for a microphone in the cerumen protection system, at the tip of the hearing device shell to the level of the exit of the loudspeaker signal with a cerumen protection system.

The cerumen protection system can be adapted to the presence of a microphone and if necessary designed correspondingly larger. In particular the cerumen protection system can be funnel-shaped. The funnel shape is particularly suitable for the sound passageway from the loudspeaker to the surface of the plastic mold, but however ensures an expansion of the cerumen protection system in which the microphone can be positioned, in the vicinity of the surface of the plastic mold. The funnel shape preferably comprises a conical segment which passes into a tube-like segment extending to the surface of the plastic mold. The microphone can be particularly easily accommodated in the tube-like segment. In this case, the microphone can either be arranged such that it is arranged with its membrane parallel to the sound exit orifice. Here the microphone can particularly effectively record the sound in the ear canal. Alternatively, the microphone with its microphone membrane can be arranged perpendicular to the sound exit opening. With this embodiment, a particularly space-saving arrangement is ensured particularly with the funnel shape of the cerumen protection system.

The tubular segment can be of an elliptical cross-section, i.e. the cerumen protection system can have an elliptical cross-section when it meets the surface of the plastic mold.

By way of example, a microphone with a circular cross-section can then be fitted particularly into the ellipse shape.

BRIEF DESCRIPTION OF THE DRAWINGS

An advantageous embodiment of the invention is now described with reference to the drawing, in which.

DETAILED DESCRIPTION OF THE INVENTION

The present invention relates to a hearing device according to the claims. The hearing device features a plastic mold which can be arranged in the ear. This plastic mold can be the hearing device shell of an in-the-ear hearing device or an otoplastic which can be inserted into the ear, said otoplastic pertaining to a behind-the-ear device.

The interior of the hearing device features a loudspeaker.

A cerumen protection system extends from the loudspeaker to the surface of the plastic mold. A cerumen protection system serves to protect the loudspeaker from the penetration of the cerumen. It creates a path for the sound from the loudspeaker to the plastic mold without cerumen being able to reach the loudspeaker.

Figure 1:
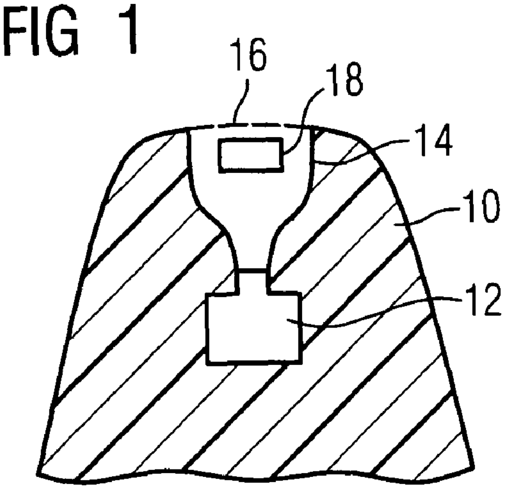
FIG. 1 shows the tip of an in-the-ear hearing device according to the invention in a lateral cross-section.

With an in-the-ear hearing device according to the invention, the hearing device is accommodated in a plastic mold, in a so-called hearing device shell. The plastic mold features a tip, which is inserted into the ear canal. Such a tip 10 of an in-the-ear hearing device according to the invention is shown in a lateral section in FIG. 1. A loudspeaker 12 is provided on the tip 10. The opening of the loudspeaker 12 is not directly positioned on the surface of the plastic mold. To protect the loudspeaker from cerumen (ear wax), a cerumen protection system 14 is provided, which is shown here in a funnel-shape. The funnel shape comprises a small plug-like tubular section below, then an expanding section, which in particular can also be conical, and then another tubular section, which extends to the surface of the plastic mold 10.

A protective membrane 16 is provided on the surface of the plastic mold across the sound exit orifice and/or the cerumen protection system, said protective membrane 16 being shown here as an open-pore membrane, but it can also be a closed protective membrane.

The upper tubular segment of the cerumen protection system creates the space for accommodating a microphone 18.

The microphone 18 is arranged here such that it extends in parallel to the surface of the plastic mold and thus in parallel to the protective membrane, with the microphone being defined above all by its microphone sound recording surface (e.g. the membrane which is not shown separately) which is arranged in parallel to the protective membrane.

Figure 2:
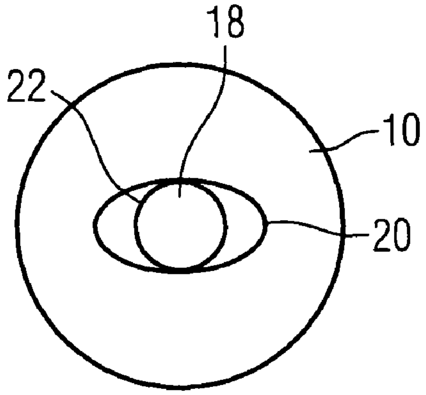
FIG. 2 shows a top view on the tip according to FIG. 1.

FIG. 2 shows a top view on the tip 10 of the plastic mold of the in-the-ear hearing device according to the invention. The tubular segment of the funnel shape 14 is shown here in particular in an elliptical cross-section on the surface of the tip 10 in the plastic mold. The ellipse shape is shown by the number 20. The microphone 18 conforms to a circular contour 22 in the ellipse shape 20.

Sufficient space is still available by virtue of the ellipse shape to ensure the exit of the sound coming from the loudspeaker 12. At the same time, the sound given off in the ear canal can be recaptured by the microphone 18 in the ear canal.

Figure 3:
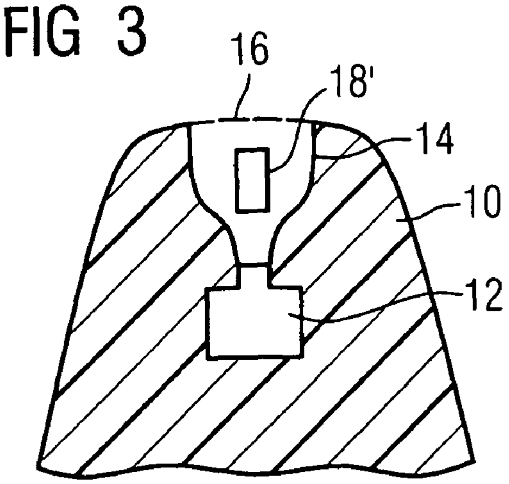
FIG. 3 shows an alternative embodiment of the tip of an in-the-ear hearing device according to the invention in a lateral cross-section.

FIG. 3 shows an alternative embodiment of the in-the-ear hearing device according to the invention. Identical parts of the tip 10 of the in-the-ear hearing device according to the invention are provided with the same reference characters. The embodiment according to FIG. 3 differs from that in FIG. 1 in terms of the orientation of the microphone, which is labeled 18' in this Figure. The microphone 18' extends here over the length of the tubular segment of the funnel shape, which is given by the cerumen protection system 14. In particular, the sound recording surface (membrane) of the microphone 18' essentially runs perpendicular to the protective membrane 16 and thus to the surface of the tip 10 of the plastic mold.

The microphone can be designed as an especially small sound recorder, which qualitatively fails to achieve the level of conventional ear canal microphones.

The invention assumes the fact that adequate space is available in the cerumen protection system to accommodate the microphone. In this case, the cerumen protection system is adapted to the special requirements relating to accommodating the microphone. The displayed funnel shape with an extending segment and subsequent tubular segment is particularly suitable for accommodating a microphone.

The invention claimed is:

1. A hearing device, comprising:

a plastic mold sized and configured for insertion in a human ear;

a sound exit orifice located in the plastic mold;

a cerumen protection system located in the sound exit orifice; and a microphone located in the cerumen protection system;

wherein a cross-section of the microphone is smaller than a cross-section of the cerumen protection system upon positioning said microphone within the sound exit orifice.

2. The hearing device as claimed in claim 1, wherein the hearing device is an in-the-ear hearing device with the plastic mold being a hearing device shell.

3. The hearing device as claimed in claim 1, wherein the hearing device is a behind-the-ear hearing device with the plastic mold being an otoplastic which is inserted into the human ear.

4. The hearing device as claimed in claim 1, wherein the cerumen protection system is closed off on a surface of the plastic mold by an open-pore membrane.

5. The hearing device as claimed in claim 1, wherein the cerumen protection system is closed off on a surface of the plastic mold by a closed protective membrane.

6. The hearing device as claimed in claim 1, wherein the cerumen protection system has a funnel-shape.

7. The hearing device as claimed in claim 6, wherein the cerumen protection system comprises a conical segment which passes into a tubular segment extending to a surface of the plastic mold.

8. The hearing device as claimed in claim 7, wherein the microphone is in the tubular segment of the cerumen protection system with a microphone sound recording surface arranged parallel to the sound exit orifice.

9. The hearing device as claimed in claim 7, wherein the microphone is in the tubular segment of the cerumen protection system with a microphone sound recording surface arranged perpendicular to the sound exit orifice.

10. The hearing device as claimed in claim 1, wherein the cerumen protection system has an elliptical cross-section.

11. The hearing device as claimed in claim 1, wherein the microphone has a circular cross-section.

12. The hearing device as claimed in claim 1, wherein the plastic mold has a tip which is inserted into a human ear canal.

13. A method for making a hearing device, comprising:

providing a plastic mold for insertion in a human ear;

arranging a sound exit orifice within the plastic mold;

arranging a cerumen protection system within the sound exit orifice; and arranging a microphone within the cerumen protection system; and adjusting a cross-section of the microphone to be smaller than a cross-section of the cerumen protection system.

14. The method as claimed in claim 13, wherein the cerumen protection system has a funnel-shape.

15. The method as claimed in claim 13, wherein the plastic mold has a tip which is inserted into a human ear canal.

* * * * *